Figures 1A, 1B:
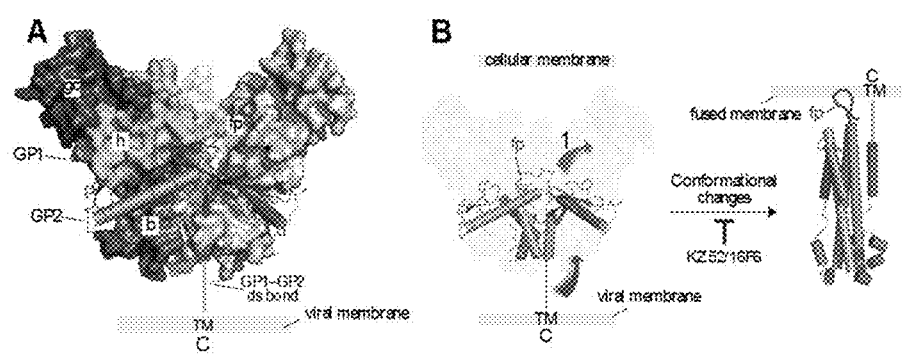

United States Patent
Lai et al.

(10) Patent No.: US 10,081,669 B2
(45) Date of Patent: Sep. 25, 2018

(54) THERAPY FOR FILOVIRUS INFECTION

(71) Applicant: ALBERT EINSTEIN COLLEGE OF MEDICINE, INC., Bronx, NY (US)

(72) Inventors: **Jonath

Fig. 2

Fig. 3

```
HEAVY CHAIN   5           11              21      -HCDR1-           41        ---HCDR2---            61            71
YADS1        evqlvesggg  lvqpggslrl  scaasgfdly  dddihwvrqa  pgkglewvay iapsyygtdy adsvkgrfti sadtskntay
16F6
CHIMERA HEAVY CHAIN   85          91----HCDR3----                    LIGHT CHAIN  5          11             21         -LCDR1
YADS1        lqmnslraed  tavyycsras  dasysyeamd  ywggtlvtv   YADS1        diqmtqspss lsasvgdrvt itcrasqasy ssvawyqqkp
16F6                               yqns---ff                 16F6
CHIMERA                            yqns---xxd                CHIMERA LIGHT CHAIN   45   LCDR2                          71         81      -LCDR3-          101
YADS1        gkapkliya asylyegvps rfsgsgsgtd ftitiselqp edfatyycq- qsaspatigq gtkvei
16F6                                                                 hystlga
CHIMERA                                         xxxxx
```

THERAPY FOR FILOVIRUS INFECTION

CROSS-REFERENCE TO RELATED APPLICATIONS

This application claims benefit of U.S. Ser. No. 14/291,608, filed May 30, 2014, which claims benefit of U.S. Provisional Application No. 61/830,325 filed Jun. 3, 2013, the contents of each of which are hereby incorporated by reference.

STATEMENT OF GOVERNMENT SUPPORT

This invention was made with government support under grant number R01-AI090249 awarded by the National Institutes of Health. The government has certain rights in the invention.

BACKGROUND OF THE INVENTION

Throughout this application, various publications are referred to in parentheses. Full citations for these references may be found at the end of the specification. The disclosures of these publications, and all patents, patent application publications and books referred to herein are hereby incorporated by reference in their entirety into the subject application to more fully describe the art to which the subject invention pertains.

Ebola virus (EBOV) pathogenesis and cell entry: The infectious agents EBOV and Marburg virus (MARV) are the two major species of the Filoviridae family of enveloped negative-sense RNA viruses (1-4). Based on nucleotide sequence and outbreak location, isolates in the EBOV species are classified into five species: Zaire (ZEBOV), Tai Forest (TAFV), Sudan (SUDV), Reston (RESTV), and Bundibugyo (BDBV). There are two MARV variants (Marburg and Ravn). Severe human disease and deaths (30-90% case fatality rates in large outbreaks) are associated with ZEBOV, SUDV, BDBV, and MARV (2). Although the ecology of these agents remains incompletely understood, several species of African fruit bats may be reservoirs for EBOV and MARV (5). ZEBOV and SUDV are the most pathogenic among the ebolaviruses, and are the only two that have been associated with recurring outbreaks (6). Among the 13 documented ZEBOV outbreaks and the six SUDV outbreaks, the average human case fatality rates are 70% and 52%, respectively. Together, ZEBOV and SUDV account for 94% of EBOV-related deaths (6). Therefore, therapeutic agents effective against ZEBOV and SUDV would greatly reduce the threat of an EBOV pandemic.

All human outbreaks occur as a result of direct contact with infected wildlife, with subsequent person-to-person transmission, mostly through the mucosa or contaminated needles. Uncontrolled viral replication is central to EBOV/MARV-induced disease, both because it is cytopathic and because it induces dysregulation of the host immune system (2, 7, 8). Therefore, antiviral therapies that reduce viral load are expected to increase patient survival, in part, by allowing time to mount an effective immune response. While many cell types can be infected with EBOV/MARV in vitro and in vivo, antigen-presenting cells (macrophages and dendritic cells) appear to be early and sustained targets of infection in vivo. Infected macrophages are unable to stimulate a robust immune response, and cause a "cytokine storm" that is proposed to be the primary cause of the bloodclotting abnormalities and vascular leakage characteristic of EBOV/MARV hemorrhagic fever (9). Damage to other tissues (e.g., liver, kidneys, vascular endothelia) is thought to contribute to the above and to late-stage multi-organ failure. Death typically occurs 8-15 days after infection (10). Because of their high mortality rate, rapid proliferation, and potential for aerosolization, EBOV and MARV are classified as Category A biodefense pathogens. There are currently no FDA-approved treatments for EBOV or MARV infection.

The EBOV/MARV genome is a ~19 kb single-strand negative-sense RNA genome that encodes seven genes arranged in a linear fashion (1-4). In mature viral particles and infected cells, the genome is intimately associated with four viral proteins: the nucleocapsid protein NP, the polymerase L, the polymerase accessory protein VP35, and the transcriptional activator protein VP30. This nucleocapsid structure is in turn encapsidated in a viral matrix, comprising proteins VP40 and VP24. The host-derived viral membrane bilayer surrounds, and is peripherally associated with, the matrix. Embedded in the viral membrane are trimers of the viral glycoprotein, GP, which mediates the first step in infection: delivery of the viral nucleocapsid "payload" into the cytoplasm of the host cell. GP is the target of virus-directed antibodies that neutralize extracellular filovirus particles (4, 11-14).

The mature EBOV/MARV GP spike is a trimer of three disulfide-linked GP1-GP2 heterodimers, generated by endo-proteolytic cleavage of the GP0 precursor polypeptide by furin during virus assembly (4, 13-15). GP1 mediates viral adhesion to host cells and regulates the activity of the transmembrane subunit GP2, which mediates fusion of viral and cellular membranes during cell entry. The prefusion GP1-GP2 spike has a "chalice-and-bowl" morphology—the three GP2 subunits form the chalice within which the bowl, comprised of the three GP1 subunits, rests (FIG. 1A) (13-15). This trimeric assembly is stabilized mainly by GP1-GP2 and GP2-GP2 contacts. The GP1 subunit is organized into three subdomains. The base ('b', light blue) interacts extensively with GP2 and clamps it in its prefusion conformation. The head ('h', green) contains a putative receptor-binding sequence. Together with GP2, the base and head subdomains of GP1 form the conserved structural core of the GP1-GP2 spike. In contrast to the GP1-GP2 core, the most external subdomains of GP1—the glycan cap ('gc', dark blue) and the mucin-like domain (not shown)—are extensively glycosylated and display a high degree of sequence variation among filovirus isolates. In response to a fusion trigger within host cell endosomes, GP2 disengages from GP1 and undergoes a series of large-scale conformational changes that drive coalescence of viral and cellular membrane bilayers (FIG. 1B) (4, 16-19). The result of viral membrane fusion is cytoplasmic release of the viral nucleocapsid. Neutralizing antibodies likely function by inhibiting these fusion-associated conformational changes (4, 13, 14).

The present invention addresses a need for improved treatments based on antibodies for filovirus infections.

SUMMARY OF THE INVENTION

The present invention addresses a need for improved treatments for filovirus infections.

This invention provides an isolated humanized anti-filovirus glycoprotein pre-fusion core antibody comprising a framework region having a sequence of 95% or greater identity to a human antibody framework region, and comprising
(a) (i) one or more of the following: a heavy chain CDR1 comprising GFAFNYYDM/I/LH (SEQ ID NO:1); a heavy chain CDR2 comprising YINPGGGNTYYADSV (SEQ ID NO:2); and a heavy chain CDR3 comprising QLYGNSF-MDY (SEQ ID NO:3), or (ii) a heavy chain CDR3 comprising QLYGNSFFDY (SEQ ID NO:4), a heavy chain CDR1 comprising SEQ ID NO:1 or GFAFNYYDMF (SEQ ID NO:17), and a heavy chain CDR2 comprising SEQ ID NO:2, and (b) a light chain sequence, comprising a light chain CDR1, CDR2 and CDR3, wherein the light chain CDR3 comprises HYSTPLT (SEQ ID NO:5).

Also provided is an isolated humanized anti-filovirus glycoprotein pre-fusion core antibody comprising a framework region having a sequence of 95% or greater identity to a human antibody framework region, and comprising (a) one or more of the following: a heavy chain CDR1 comprising GFAFNYYDMF (SEQ ID NO:17), a heavy chain CDR2 comprising YINPGGGNTYYPDSV (SEQ ID NO:18), a heavy chain CDR3 comprising QLYGNSFFDY (SEQ ID NO:19) and comprising (b) a light chain sequence, comprising at least (i) a light chain CDR3, which comprises HYSTPLT (SEQ ID NO:5) and (ii) comprising DIQMTQSPSSLSASVGDRVTITCKASQDVTTAVAWYQQKPGKAPKL (SEQ ID NO:20) and either (i) LIYAASGRYIGVPSRFSGSGSGTDFTLTISSLQPEDFATYYCQQ (SEQ ID NO:21) or (ii) LIYAASFLHRGVPSRFSGSGSGTDFTLTISSLQPEDFATYYCQQ (SEQ ID NO:22).

Also provided is an antigen-binding fragment of any of the antibodies described herein.

Also provided is composition comprising any of the antibodies described herein or the antigen-binding fragments described herein. In an embodiment, the composition comprises a pharmaceutically acceptably carrier.

Also provided is a method of treating a filovirus infection in a subject comprising administering to the subject an amount of any of the antibodies described herein, or an amount of any of the antigen-binding fragments described herein or an amount of any of the compositions described herein effective to treat a filovirus infection in a subject.

Also provided is a method of inhibiting a filovirus infection of a subject comprising administering to the subject an amount of any of the antibodies described herein, or an amount of any of the antigen-binding fragments described herein or an amount of any of the compositions described herein effective to inhibit a filovirus infection in a subject.

BRIEF DESCRIPTION OF THE DRAWINGS

FIGS. 1A-1B: Structure of the pre-fusion GP1-GP1 spike and GP conformational changes that lead to viral membrane fusion. FIG. 1A shows the structure of the GP1-GP2 spike ectodomain (PDB ID: 3CSY, ref 13). The GP1 subunits are shown in surface-shaded view and GP2 as rods and loops. One GP1 subunit is colored to show the subdomains: b, base; h, head; gc, glycan cap. fp, fusion peptide. TM, transmembrane domain. C, GP C-terminus. FIG. 1B shows membrane fusion-associated conformational rearrangements in GP2 inferring from its pre-fusion and putative post-fusion structures (PDB ID: 1EBO, ref 17).

FIG. 2: Survival of NHPs administered ZEBOV-specific serum IgGs upon viral challenge. Animals 7, 8, and 9 survived but the control animal (5) died 8-days post-exposure. These data are from ref. 21 (Dye et al.).

FIG. 3: Head-to-head comparison of KZ52 IgG against VSV-GPZEBOV and 16F6 IgG against VSV-GPSUDV.

FIG. 4: Sequence alignment of YADS1 (an optimized Herceptin-based framework) and 16F6. The "chimera" represents the 16F6 CDR segments grafted on to the YADS1 scaffold. Residues identical to YADS1 shown in gray for 16F6 and the chimera. Sites of randomization in the humanization library indicated by 'x' on the chimera and highlighted. YADS1 Heavy Chain with CDR1 and CDR2 is SEQ ID NO:23; 16F6 Heavy Chain with CDR1 and CDR2 is SEQ ID NO:24; CHIMERA Heavy Chain with CDR1 and CDR2 is SEQ ID NO:25; YADS1 Heavy Chain with CDR3 is SEQ ID NO:26; 16F6 Heavy Chain with CDR3 is SEQ ID NO:27; CHIMERA Heavy Chain with CDR3 is SEQ ID NO:28; YADS1 Light Chain with CDR1 is SEQ ID NO:29; 16F6 Chain with CDR1 is SEQ ID NO:30; CHIMERA Light Chain with CDR1 is SEQ ID NO:31; YADS1 Light Chain with CDR2 and CDR3 is SEQ ID NO:32; 16F6 Light Chain with CDR2 and CDR3 is SEQ ID NO:33; CHIMERA Light Chain with CDR2 and CDR3 is SEQ ID NO:34.

FIG. 5: Structural alignment of YADS1 (cyan) and 16F6 (raspberry) variable domains.

Figures 6A, 6B:
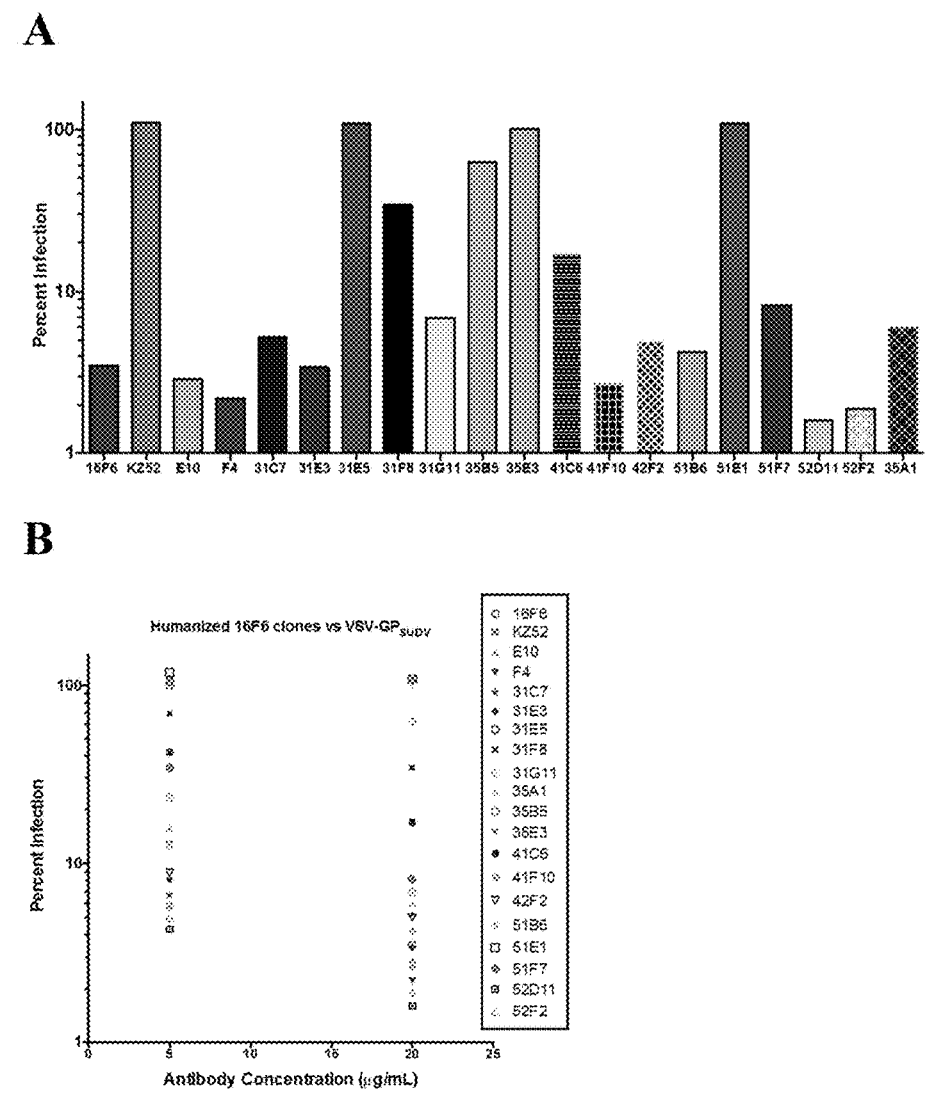

FIGS. 6A-6B: Neutralization activity against VSV-GP-SUDV. (A) Histogram plot of activity at 20 μM mAb concentration; (B) scatter plot at 5 μM or 20 μM mAb. Many of the humanized variants performed as well or better than 16F6. Twelve of the mAbs showed greater than 90% neutralization at 20 μM.

FIG. 7A-B: ELISA binding of E10 (FIG. 7A) and F4 (FIG. 7B) against GP from SUDV (Sudan) (filled circles), ZEBOV (Zaire), or 5% non-fat dry milk (NFDM) (triangles and squares).

FIG. 8: Sudan virus challenge dosing in mice: 500 ug of mAb/mouse at days (−1), (+1), and (+4)

FIG. 9: Re-challenge of surviving mice from FIG. 8.

FIG. 10: Challenge dosing: 500 ug of mAb/mouse at days (+1), and (+4). This experiment tests the "post-exposure" potential of the mAbs.

DETAILED DESCRIPTION OF THE INVENTION

This invention provides an isolated humanized anti-Filovirus glycoprotein pre-fusion core antibody comprising a framework region having a sequence of 95% or greater identity to a human antibody framework region, and comprising (a) (i) one or more of the following: a heavy chain CDR1 comprising GFAFNYYDM/I/LH (SEQ ID NO:1); a heavy chain CDR2 comprising YINPGGGNTYYADSV (SEQ ID NO:2); and a heavy chain CDR3 comprising QLYGNSFMDY (SEQ ID NO:3), or (ii) a heavy chain CDR3 comprising QLYGNSFFDY (SEQ ID NO:4), a heavy chain CDR1 comprising SEQ ID NO:1 or GFAFNYYDMF (SEQ ID NO:17), and a heavy chain CDR2 comprising SEQ ID NO:2, and (b) a light chain sequence, comprising a light chain CDR1, CDR2 and CDR3, wherein the light chain CDR3 comprises HYSTPLT (SEQ ID NO:5).

In an embodiment, the heavy chain comprises the sequence EVQLVESGGGLVQPGGSLRLSCAASGFAFNYYDIHWVRQAPGKGLE (SEQ ID NO:6) or EVQLVESGGGLVQPGGSLRLSCAASGFAFNYYDLHWVRQAPGKGLE (SEQ ID NO:7) or EVQLVESGGGLVQPGGSLRLSCAASGFAFNYYDMHWVRQAPGKGLE (SEQ ID NO:8). In an embodiment, the heavy chain comprises the sequence WVAYINPGGGNTYYADSVKGRFTISADTSKNTAYLQMNSLRAEDTA (SEQ ID NO:9). In an embodiment, the heavy chain comprises the sequence VYYCARQLYGNSFMDYWGQGTLVTV (SEQ ID NO:10) or VYYCARQLYGNSFFDYWGQGTLVTV (SEQ ID NO:11). In an embodiment, the light chain comprises the sequence

DIQMTQSPSSLSASVGDRVTITCK/R/QASQDVT-
TAVAWYQQKPGKAPKL (SEQ ID NO:12).

In an embodiment, the light chain comprises the sequence LIYAASGRHKGVPSRFSGSGSGTDFTLTISSLQPEDFA-TYYCQQ (SEQ ID NO:13) or LIYAASRLHNGVPSRF-SGSGSGTDFTLTISSLQPEDFATYYCQQ (SEQ ID NO:14) or LIYAASTRHTGVPSRFSGSGSGTDFTLTISS-LQPEDFATYYCQQ (SEQ ID NO:15). In an embodiment, the light chain comprises the sequence HYSTPLTFGQGT-KVFI (SEQ ID NO:16).

Also provided is an isolated humanized anti-filovirus glycoprotein pre-fusion core antibody comprising a framework region having a sequence of 95% or greater identity to a human antibody framework region, and comprising (a) one or more of the following: a heavy chain CDR1 comprising GFAFNYYDMF (SEQ ID NO:17), a heavy chain CDR2 comprising YINPGGGNTYYPDSV (SEQ ID NO:18), a heavy chain CDR3 comprising QLYGNSFFDY (SEQ ID NO:19) and comprising (b) a light chain sequence, comprising at least (i) a light chain CDR3, which comprises HYSTPLT (SEQ ID NO:5) and (ii) comprising DIQMTQSPSSLSASVGDRVTITCKASQDVTTAVAWY-QQKPGKAPKL (SEQ ID NO:20) and either (i) LIYAAS-GRYIGVPSRFSGSGSGTDFTLTISSLQPEDFATYYCQQ (SEQ ID NO:21) or (ii) LIYAASFLHRGVPSRFSGSGS-GTDFTLTISSLQPEDFATYYCQQ (SEQ ID NO:22).

Also provided is an antigen-binding fragment of any of the antibodies described herein.

Also provided is composition comprising any of the antibodies described herein or the antigen-binding fragments described herein. In an embodiment, the composition comprises a pharmaceutically acceptably carrier.

Also provided is a method of treating a filovirus infection in a subject comprising administering to the subject an amount of any of the antibodies described herein, or an amount of any of the antigen-binding fragments described herein or an amount of any of the compositions described herein effective to treat a filovirus infection in a subject.

Also provided is a method of inhibiting a filovirus infection of a subject comprising administering to the subject an amount of any of the antibodies described herein, or an amount of any of the antigen-binding fragments described herein or an amount of any of the compositions described herein effective to inhibit a filovirus infection in a subject.

In an embodiment of the methods, the antibody, antigen-binding fragment or composition are administered prior to the subject being exposed to the filovirus. In an embodiment of the methods, the antibody, antigen-binding fragment or composition are administered after the subject has been exposed to the filovirus. In an embodiment of the methods, the filovirus is an Ebola virus. In an embodiment of the methods, the Ebola virus is the Sudan strain. In an embodiment of the methods, the filovirus is a Marburg virus. In an embodiment of the methods, the filovirus is not a Marburg virus.

In an embodiment of any of the antibodies described herein, or any of the antigen-binding fragments described herein or any of the compositions described herein, or the methods described herein, the antibody is a neutralizing antibody. In an embodiment, the pre-fusion core is a heterohexamer of three copies of the GP1 and 3 copies of the GP2.

In an embodiment, the isolated antibody or antigen-binding antibody fragment comprises an Fc region having a sequence identical to a human Fc region.

In an embodiment, the Fc region of the antibody is glycosylated.

A "humanized" antibody as used herein, unless otherwise indicated, is a chimeric antibodies that contain minimal sequence (CDRs) derived from non-human immunoglobulin (e.g. such as a mouse immunoglobulin). In one embodiment, a humanized antibody is an antibody having a sequence of a human immunoglobulin (recipient antibody) in which CDR residues of a hypervariable region (HVR) of the recipient are replaced by CDR residues from a non-human species (donor antibody) such as a mouse having the desired specificity. In some instances, FR residues of the human immunoglobulin variable domain are replaced by corresponding non-human residues, for example by a back-mutation. In general, a humanized antibody will comprise substantially all of at least one, and typically two, variable domains, in which all or substantially all of the hypervariable loops correspond to those of a non-human immunoglobulin, and all or substantially all of the FRs are those of a human immunoglobulin sequence. The humanized antibody optionally will also comprise at least a portion of an immunoglobulin constant region (Fc), typically that of a human immunoglobulin. See, e.g., Jones et al., Nature 321:522-525 (1986); Riechmann et al., Nature 332:323-329 (1988); Presta, Curr. Op. Struct. Biol. 2:593-596 (1992); Vaswani and Hamilton, Ann. Allergy, Asthma & Immunol. 1:105-115 (1998); Harris, Biochem. Soc. Transactions 23:1035-1038 (1995); Hurle and Gross, Curr. Op. Biotech. 5:428-433 (1994); and U.S. Pat. Nos. 6,982,321 and 7,087,409, the contents of each of which references and patents are hereby incorporated by reference in their entirety. Other techniques to humanize a monoclonal antibody are described in U.S. Pat. Nos. 4,816,567; 5,807,715; 5,866,692; 6,331,415; 5,530,101; 5,693,761; 5,693,762; 5,585,089; and 6,180,370, the content of each of which is hereby incorporated by reference in its entirety. The framework regions of the antibodies of the invention having a sequence identical to a human framework region may include amino acid residues not encoded by human germline sequences (e.g., mutations introduced by random or site-specific mutagenesis). In an embodiment, the isolated antibody or antigen-binding antibody fragment comprises a variable domain framework sequence having a sequence identical to a human variable domain framework sequence FR1, FR2, FR3 or FR4. In an embodiment, the isolated antibody or antigen-binding antibody fragment comprises a variable domain framework sequence having a sequence identical to at least two of human variable domain framework sequences FR1, FR2, FR3 or FR4. In an embodiment, the isolated antibody or antigen-binding antibody fragment comprises a variable domain framework sequence having a sequence identical to at least three of human variable domain framework sequences FR1, FR2, FR3 or FR4. In an embodiment, the isolated antibody or antigen-binding antibody fragment comprises a variable domain framework sequence having a sequence identical to all four of human variable domain framework sequences FR1, FR2, FR3 and FR4.

An isolated nucleic acid is provided encoding a VH or a VL of the antibodies, or fragments thereof, as described herein. In an embodiment, the isolated nucleic acid is a DNA. In an embodiment, the isolated nucleic acid is a cDNA. In an embodiment, the isolated nucleic acid is a RNA. A recombinant nucleic acid encoding an antibody as described herein is also provided. Also provided is a cell, wherein the cell is not in a human subject, transformed with the recombinant nucleic acid. In an embodiment, the cell is a mammalian cell. In an embodiment, the cell is derived from a human but is not in a human subject. In an embodiment, the cell is not a human cell.

As used herein, "at least 95% identical to" encompasses a sequence that has at least 95%, 96%, 97%, 98% or 99% identity with, or is 100% identical to, the referenced sequence. Accordingly, the individual embodiments of at least 95% identical to, at least 96% identical to, at least 97% identical to, at least 98% identical to, at least 99% identical to, and 100% identical to, are each all separately encompassed by the invention.

The antigen, in regard to the term "antigen-binding fragment" as used herein, is a Filovirus glycoprotein pre-fusion core.

In an embodiment of the antibodies, fragments, methods and compositions described herein, the fragment of the antibody comprises an Fab, an Fab', an F(ab')2, an Fd, an Fv, or a complementarity determining region (CDR). In an embodiment, the fragment comprises a CDR3 of a VH chain. In an embodiment the fragment further comprises one of, more than one of, or all of CDR1, CDR2 of Vh and CDR1, CDR2 and CDR3 of a VL. As used herein, an Fd fragment means an antibody fragment that consists of the VH and CH1 domains; an Fv fragment consists of the VL and VH domains of a single arm of an antibody; and a dAb fragment (Ward et al., Nature 341:544-546 (1989) hereby incorporated by reference in its entirety) consists of a VH domain. In some embodiments, fragments are at least 5, 6, 8 or 10 amino acids long. In other embodiments, the fragments are at least 14, at least 20, at least 50, or at least 70, 80, 90, 100, 150 or 200 amino acids long.

In an embodiment, the fragment of the antibody encompassed by the invention is a single-chain antibody (scFv) is a variable domain light chain (VL) and a variable domain heavy chain (VH) which are linked N—C or C—N, respectively, via a peptide linker. In an embodiment the linker of the scFv is 5-30 amino acids in length. In an embodiment the linker of the scFv is 10-25 amino acids in length. In an embodiment the peptide linker comprises glycine, serine and/or threonine residues. For example, see Bird et al., Science, 242: 423-426 (1988) and Huston et al., Proc. Natl. Acad. Sci. USA, 85:5879-5883 (1988), each of which are hereby incorporated by reference in their entirety. In an embodiment, the fragment of the antibody of the invention is not a single-chain antibody (scFv).

The term "Fc region" herein is used to define a C-terminal region of an immunoglobulin heavy chain, including native sequence Fc regions and variant Fc regions. Although the boundaries of the Fc region of an immunoglobulin heavy chain might vary, the human IgG heavy chain Fc region is often defined to stretch from an amino acid residue at position Cys226, or from Pro230, to the carboxyl-terminus thereof. The C-terminal lysine of the Fc region may be removed, for example, during production or purification of the antibody, or by recombinantly engineering the nucleic acid encoding a heavy chain of the antibody. Accordingly, an intact antibody as used herein may be an antibody with or without the otherwise C-terminal cysteine.

In an embodiment, the antibodies of the invention described herein comprise a human Fc region or a variant human Fc region. A variant human Fc region comprises an amino acid sequence which differs from that of a native sequence Fc region by virtue of at least one amino acid modification, yet retains at least one effector function of the native sequence human Fc region. Preferably, the variant Fc region has at least one amino acid substitution compared to a native sequence Fc region or to the Fc region of a parent polypeptide, e.g. from about one to about ten amino acid substitutions, and preferably, from about one to about five amino acid substitutions in a native sequence Fc region or in the Fc region of the parent polypeptide. The variant Fc region herein will preferably possess at least about 80% sequence identity with a native sequence Fc region and/or with an Fc region of a parent polypeptide, and most preferably, at least about 90% sequence identity therewith, more preferably, at least about 95%, at least about 96%, at least about 97%, at least about 98%, at least about 99% sequence identity therewith.

Although the boundaries of the Fc region of an immunoglobulin heavy chain might vary, the human IgG heavy chain Fc region is often defined to stretch from an amino acid residue at position Cys226, or from Pro230, to the carboxyl-terminus thereof. The C-terminal lysine of the Fc region may be removed, for example, during production or purification of the antibody, or by recombinantly engineering the nucleic acid encoding a heavy chain of the antibody. Accordingly, an intact antibody as used herein may be an antibody with or without the otherwise C-terminal cysteine.

In an embodiment of the methods, the antibody, antibodies, antibody fragment or antibody fragments are administered as an adjuvant therapy to a primary therapy for the disease or condition.

The invention also provides diagnostic kits comprising any or all of the antibodies described herein. The diagnostic kits are useful for, for example, detecting the presence of a filovirus in a sample.

The humanized antibodies of the invention exclude any antibodies that naturally occur in a human.

As used herein, the term "isolated antibody" refers to an antibody that by virtue of its origin or source of derivation has one to four of the following characteristics: (1) is not associated with naturally associated components that accompany it in its native state, (2) is free of other proteins from the same species, (3) is expressed by a cell from a different species, or (4) does not occur in nature.

The phrase "and/or" as used herein, with option A and/or option B for example, encompasses the embodiments of (i) option A, (ii) option B, and (iii) option A plus option B.

It is understood that wherever embodiments are described herein with the language "comprising," otherwise analogous embodiments described in terms of "consisting of" and/or "consisting essentially of" are also provided.

Where aspects or embodiments of the invention are described in terms of a Markush group or other grouping of alternatives, the present invention encompasses not only the entire group listed as a whole, but each member of the group subjectly and all possible subgroups of the main group, but also the main group absent one or more of the group members. The present invention also envisages the explicit exclusion of one or more of any of the group members in the claimed invention.

All combinations of the various elements described herein are within the scope of the invention unless otherwise indicated herein or otherwise clearly contradicted by context.

In the event that one or more of the literature and similar materials incorporated by reference herein differs from or contradicts this application, including but not limited to defined terms, term usage, described techniques, or the like, this application controls.

This invention will be better understood from the Experimental Details, which follow. However, one skilled in the art will readily appreciate that the specific methods and results discussed are merely illustrative of the invention as described more fully in the claims that follow thereafter.

EXPERIMENTAL RESULTS

Introduction

Figure 2:
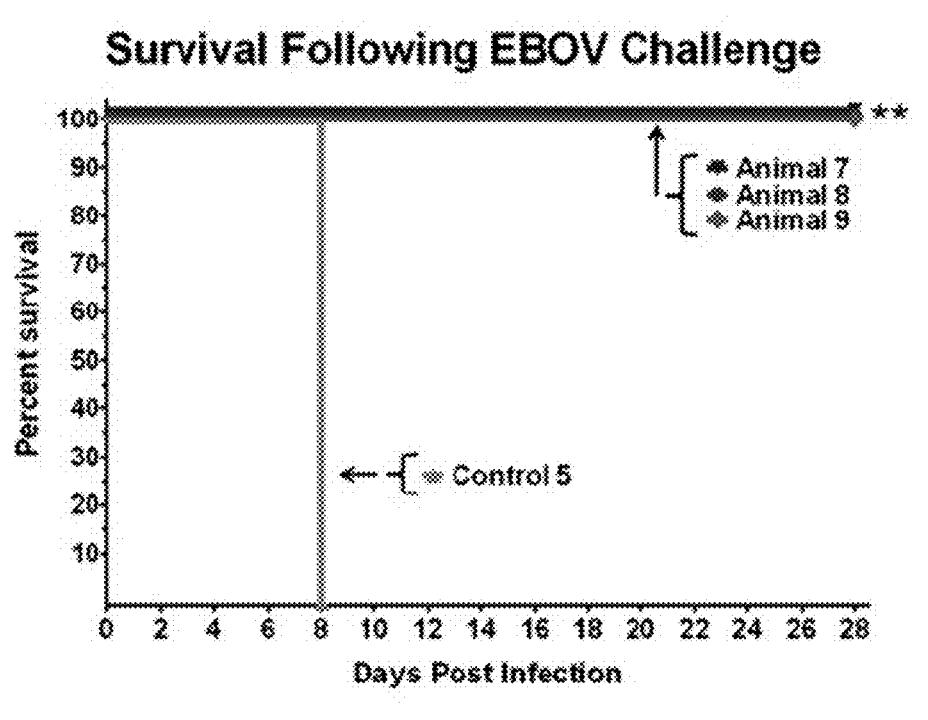

Immunotherapy is a tractable approach to filovirus treatment pre- and post-exposure: Until recently, it has been unclear if passive immunotherapy would be effective for treatment or prophylaxis of filovirus infection (20). However, two recent studies using non-human primate (NHP) models have provided convincing evidence that immunotherapy can and should be pursued (21, 22). Dr. Dye's laboratory reported that NHPs can be protected up to 48 hours post-exposure from MARV or ZEBOV infection by passive transfer of fractionated ZEBOV-specific IgG, or MARV-specific IgG, isolated from convalescent animals (same species) (21). In this study, two of the three NHPs that were challenged with ZEBOV, and then administered serum IgG, had no clinical signs of illness; the third developed mild, delayed signs of the disease but fully recovered (FIG. 2). The control animal died eight days post exposure. Similar results were obtained with MARV-challenged animals, suggesting that filovirus infection in general can be treated with antibodies. This protection required only three total administrations of the serum IgG (48 hours post exposure, then again at four and eight days). Therefore, antibody-based EBOV therapy is feasible, protective, and can be administered post-exposure. Earlier this year, Marzi et al. demonstrated that a combination therapy using two human-mouse chimeric monoclonal antibodies (mAbs) could partially protect NHPs against ZEBOV challenge (22). In this study, three NHPs were administered a cocktail of the two mAbs 24 hours preceding challenge with ZEBOV, then again 24- and 48-hours post-exposure. One of the three animals survived, one had delayed onset of hemorrhagic fever and was ultimately euthanized, and the other was similar to the control. From this work, it was concluded that the protection could be improved if serum half-life of the mAbs were optimized, or if the mAbs were used in combination with other mAbs or therapies. Enhanced neutralization potency would also likely improve protection, Given these recent findings, it appears that EBOV mAb therapy can be used prophylactically and acutely following exposure in humans.

Results

EXAMPLE 1

Figure 3:
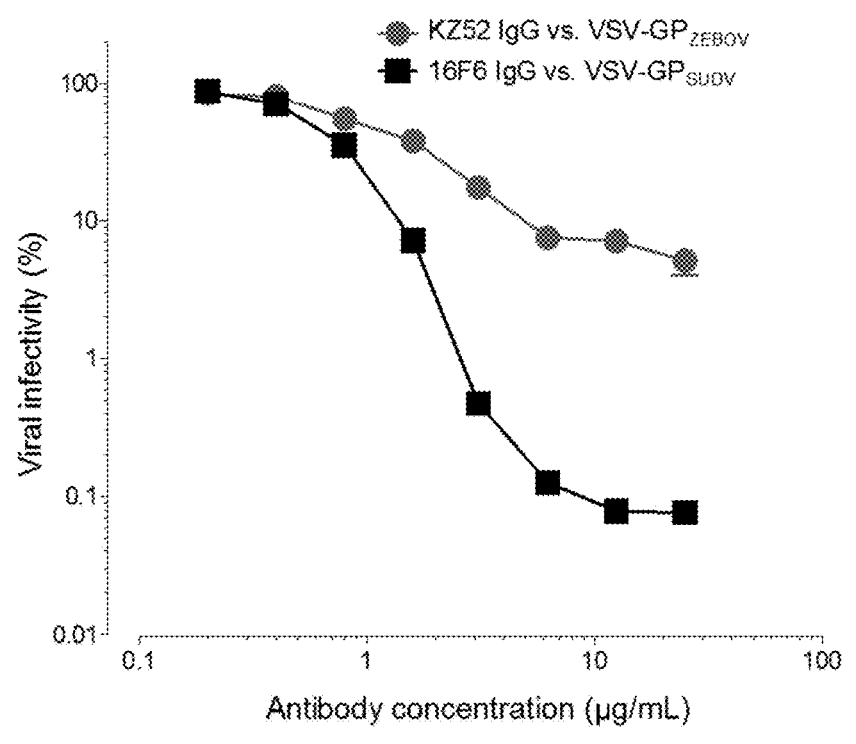

There is a gap in treatment of EBOV infection: Only a handful of animal challenge studies have been performed with mAb therapies, in part because few mAbs that target GP (the primary neutralization target) exist. Most antibodies elicited in natural infection react preferentially with a secreted, dimeric version of the glycoprotein known as sGP and do not neutralize the fusion-relevant GP spike (4, 23, 24). Wilson et al. first demonstrated that GP-specific neutralizing antibodies (nAbs) could protect mice from ZEBOV challenge (25). However, three of five protective antibodies recognize highly variable sequences within the GP1 mucin-like domain, rendering them unlikely candidates for development of cross-neutralizing mAbs. Antibodies KZ52 and 16F6 are among the few well-characterized nAbs and both bind to the GP prefusion core (elaborated further in Section 3b) (13, 14). KZ52 was identified by phage-based panning of a B-cell antibody library isolated from a human survivor of ZEBOV infection (26). Initial experiments in rodent protection studies were promising, but KZ52 failed to protect in macaques when administered on days −1 and +4 at 50 mg/kg (12, 20). However, it is possible that a more aggressive treatment regimen may provide protection. 16F6, a mouse mAb, was identified recently by Dr. Dye's group by vaccination with vector-based vaccine expressing SUDV GP (14). mAb 16F6 is much more potent than is KZ52 against the corresponding virus species, but its murine scaffold limits therapeutic utility at this point. Head-to-head comparison in neutralizations assays using a vesicular stomatitis virus pseudotype (VSV-GP) with KZ52 (against ZEBOV GP, $GP_{ZEBOV}$) and 16F6 (against SUDV GP, $GP_{SUDV}$) indicates that 16F6 can reduce infectivity by at least 10-fold more than KZ52 at high antibody concentrations (FIG. 3). The cause for this discrepancy is not clear, but these data nonetheless demonstrate that there is room for improvement in KZ52 activity. An immunocompetent mouse SUDV model is not available; however 16F6 treatment delays death of SCID mice challenged with SCID-adapted SUDV by 5-7 days (14). It is therefore likely that an optimized 16F6 variant will be protective.

Several candidate therapies and vaccines are under exploration for filovirus infection (27-33). Multiple promising vaccine candidates are able to protect NHPs from lethal challenge, including adenovirus-vectored, VSV-vectored, and virus-like particle-based vaccines (28-30). While any safe and effective EBOV vaccine will be useful for populations or workers that are at high risk for exposure, it is unlikely that vaccination against EBOV will be practical on a general population level. Therefore, there is still a need for an EBOV therapy that can be used to treat acute exposure or infection. Other biologics are under evaluation, including an antisense therapy undergoing clinical trials, and a promising RNAi therapy (31, 32). However, the use of nucleic acids as therapeutic agents in general is in its infancy and therefore there is a high barrier to FDA approval for such biologics. Furthermore, these therapeutic nucleic acids are strain-specific. Some small molecules against EBOV or host targets are also being explored, but studies are largely limited to early proof-of-concept stage (33-35). A mAb treatment has lower barriers to FDA approval than other therapeutic platforms given the broad use of mAbs in autoimmune diseases and cancer, as well as more recent use in prevention and treatment of infectious diseases (36).

Synthetic antibody engineering permits identification of antibodies with enhanced properties: Antibody phage display has emerged as a powerful alternative to hybridoma technology for the generation of mAbs (37-40). It is now possible to select high-affinity antibodies against virtually any antigen from phage libraries that bear tailored diversity elements encoded by synthetic DNA ("synthetic antibodies") (41-45). This approach obviates the requirement for human or animal immunization, greatly reducing the labor and cost of antibody production. Selective enrichment of high-affinity binders from phage antibody libraries under controlled conditions enhances the reliability of output antibodies, and permits selection of binding with user-specified stringency (45). The expression of antibody domains on the surface of bacteriophage was first reported nearly two decades ago, but only recently have synthetic libraries (where diversity is not borne from natural source repertoires) become sophisticated enough for general use. Combined empirical and bioinformatic data guide predictions of locations in the antibody complementarity determining regions (CDRs) that favor antigen recognition (38, 41). The chemical (i.e., amino acid side chain) diversity encoded at these CDR positions can then be specified with designed codon sets that reduce sequence complexity but optimize combining site properties for molecular recognition (41, 42).

Figure 5:
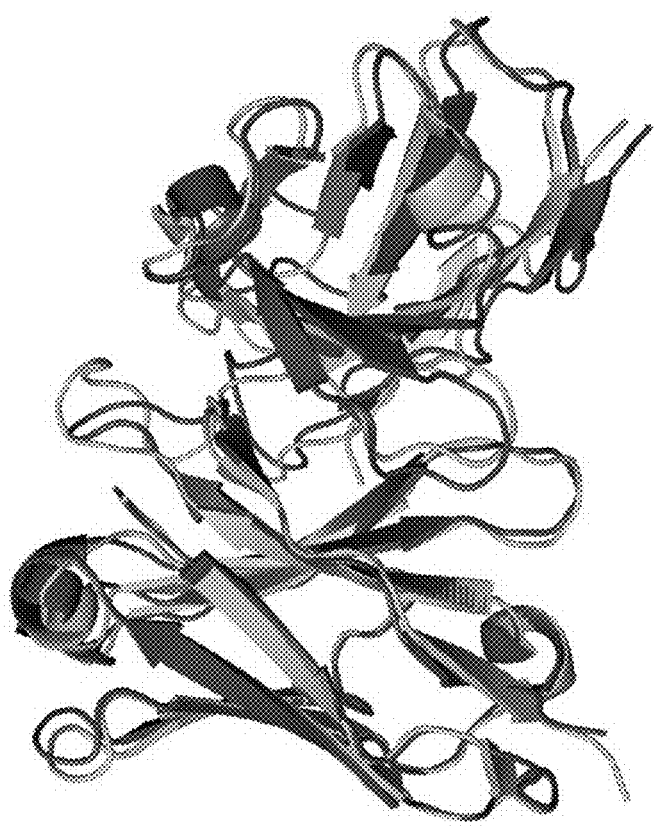

Humanizing SUDV-specific antibody 16F6 ("hu16F6"): 16F6 itself is of limited therapeutic utility because it is a murine antibody (14). (See also WO/2011/071574 for 16F6 antibodies. The contents of WO/2011/071574 are hereby incorporated by reference in their entirety). A sequence alignment of 16F6 in comparison to a synthetic antibody based on the optimized human framework of Herceptin (YADS1, ref 48) is shown in FIG. 4, and a structural alignment of the variable domains shown in FIG. 5. Notably, 16F6 and YADS1 have high homology in the framework regions and the structural alignment shows that positioning of the CDR beginning and end points is similar among the two scaffolds. This analysis suggests that 16F6 can be humanized by grafting the 16F6 CDR segments onto the YADS1 framework to produce a 16F6-YADS1 chimera Fab. A summary of the steps is as follows:

Randomization is included at framework or structural (i.e., non-contact) CDR positions in a manner that permits the residue identity of 16F6, YADS1, or side chains with similar physicochemical attributes. Two positions on the YADS1 scaffold that correspond to contacting framework residues in 16F6 (T53 and T56) are diversified to allow for all 20 genetically-encoded amino acids. The 'theoretical diversity' of this library is $4 \times 10^7$, which can be exhaustively sampled by phage display libraries that contain >$10^{10}$ unique members. Neutralization of pseudotyped virus: The humanization library in FIG. 4 was constructed and screened against soluble GP from SUDV ($GP_{SUDV}$). Binding to the target was assessed at a preliminary level by phage ELISA. The most promising clones were produced as IgGs and screened for neutralization against vesicular stomatitis virus pseudotyped with $GP_{SUDV}$ (VSV-$GP_{SUDV}$).

Neutralization of authentic SUDV: Clones E10 and F4 were tested for neutralization against authentic SUDV under BSL4 conditions at USAMRIID. E10 neutralized authentic SUDV by 80% or more at less than 0.625 µg/mL with and without complement. F4 neutralized authentic SUDV by 80% or more at less than 0.625 µg/mL with complement and 1.25 µg/mL without complement.

Figures 7A, 7B:
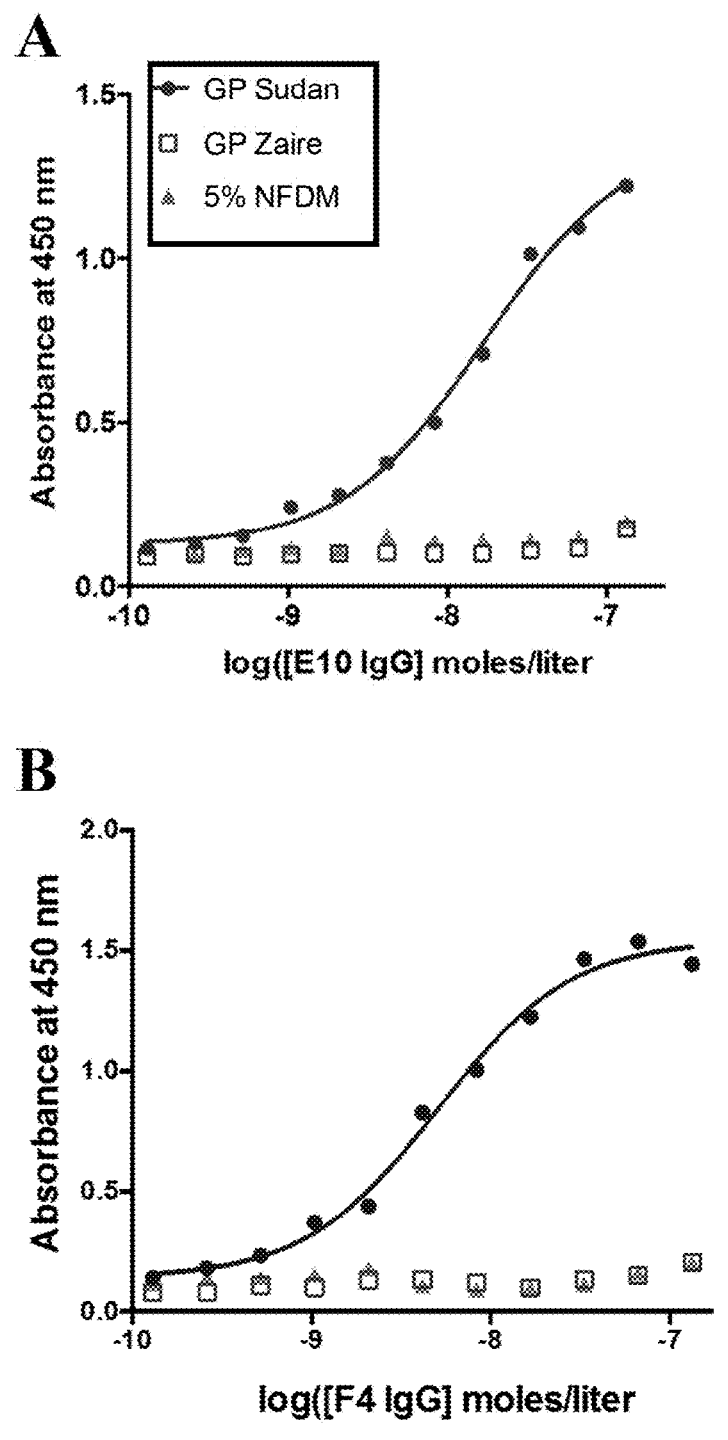

Additional Characterization of E10 and F4: Clones E10 and F4 were characterized for binding to GPSUDV by ELISA (FIG. 7). There was no cross-reactivity for GP from ZEBOV (GP Zaire) or 5% non-fat dry milk (NFDM). The half-maximal binding titers for GPSUDV were 17 nM for E10 and 5.1 nM for F4.

Sequences: The amino acid sequences of sixteen clones are shown below in alignment with 16F6 and YADS1 (only those amino acids that differ from 16F6 are shown). The CDRH1, CDRH2, CDRH3, and CDRL3 segments are underlined.

```
HEAVY CHAIN SEQUENCES:
16F6:       EVQLVESGGGLVTPGGSLKLSCAASGFAFNYYDMFWVRQNTEKRLE

YADS1:               Q       R          DIYDD IH     APG G

E10:                 Q       R                IH     APG G

F4:                  Q       R                       APG G

31C7:                Q       R                       APG G

31E3:                Q       R                       APG G

31F8:                Q       R                       APG G

31G11:               Q       R                       APG G

34F5:                Q       R                       APG G

35A1:                Q       R                       APG G

35B5:                Q       R                       APG G

41C6:                Q       R                 H     APG G

41F10:               Q       R                LH     APG G

42F2:                Q       R                       APG G

51B6:                Q       R                LY     APG G

51F7:                Q       R                       APG G

52D11:               Q       R                       APG G

52F2:                Q       R                 H     APG G

16F6:       WVAYINSGGGNTYYPDTVKGRFTISRDNAKKTLFLQMSSLRSEDTA

YADS1:         APSY Y D A S      A TS N AY   N   A

E10:              P    A S       A TS N AY   N   A

F4:               P    A S       A TS N AY   N   A

31C7:             P    A S       A TS N AY   N   A

31E3:             P      S       A TS N AY   N   A
```

```
                              -continued
31F8:                 A S       A TS N AY    N   A

31G11:         P       S        A TS N AY    N   A

34F5:                  S        A TS N AY    N   A

35A1:          P       S        A TS N AY    N   A

35B5:                  S        A TS N AY    N   A

41C6:          P      A S       A TS N AY    N   A

41F10:         P      A S       A TS N AY    N   A

42F2:          P       S        A TS N AY    N   A

51B6:          P       S        A TS N AY    N   A

51F7:                  S        A TS N AY    N   A

52D11:         P       S        A TS N AY    N   A

52F2:          P      A S       A TS N AY    N   A

16F6:      MYYCARQLYGNS---FFDYWGQGTSLTV

YADS1:         V     S SSDASYSYSAM       LV

E10:           V              M          LV

F4:            V                         LV

31C7:          V              L          LV

31E3:          V                         LV

31F8:          V                         LV

31G11:         V                         LV

34F5:          V                         LV

35A1:          V                         LV

35B5:          V                         LV

41C6:          V                         LV

41F10:         V                         LV

42F2:          V                         LV

51B6:          V                         LV

51F7:          V                         LV

52D11:         V                         LV

52F2:          V              M          LV

LIGHT CHAIN SEQUENCES:
16F6:      DIVMTQSHKFMSTSVGDRVTITCKASQDVTTAVAWYQQKPGHSPKL

YADS1:         Q     PSSL A         R    ASYSS          KA

E10:           Q     PSSL A         R                   KA

F4:            Q     PSSL A                             KA

31C7:          Q     PSSL A                             KA

31E3:          Q     PSSL A                             KA

31F8:          Q     PSSL A                             KA

31G11:         Q     PSSL A                             KA

34F5:          Q     PSSL A                             KA

35A1:          Q     PSSL A              Q             KA
```

```
                            -continued
35B5:          Q    PSSL A                        KA

41C6:          Q    PSSL A                        KA

41F10:         Q    PSSL A                        KA

42F2:          Q    PSSL A                        KA

51B6:          Q    PSSL A                        KA

51F7:          Q    PSSL A                        KA

52D11:         Q    PSSL A                        KA

52F2:          Q    PSSL A         Q              KA

16F6:     LIYWASTRHTGVPDRFTGSGSGTAFTLTLNSVQAEDLALYYCQQ
YADS1:         A    YLYS   S  S    D    IS L P   F T    -

E10:           A    RLHN   S  S    D    IS L P   F T

F4:            A           S  S    D    IS L P   F T

31C7:          A   S YP    S  S    D    IS L P   F T

31E3:          A   G YI    S  S    D    IS L P   F T

31F8:          A           S  S    D    IS L P   F T

31G11:         A   S Y     S  S    D    IS L P   F T

34F5:          A   A R     S  S    D    IS L P   F T

35A1:          A   SL F    S  S    D    IS L P   F T

35B5:          A           S  S    D    IS L P   F T

41C6:          A           S  S    D    IS L P   F T

41F10:         A           S  S    D    IS L P   F T

42F2:          A           S  S    D    IS L P   F T

51B6:          A           S  S    D    IS L P   F T

51F7:          A           S  S    D    IS L P   F T

52D11:         A   FL R    S  S    D    IS L P   F T

52F2:          A   G K     S  S    D    IS L P   F T

16F6:     HYSTPLTFGAGTKLFL
YADS1:    SSAS A    Q    V I

E10:                Q    V I

F4:                 Q    V I

31C7:               Q    V I

31E3:               Q    V I

31F8:               Q    V I

31G11:              Q    V I

34F5:               Q    V I

35A1:               Q    V I

35B5:               Q    V I

41C6:               Q    V I

41F10:              Q    V I

42F2:               Q    V I

51B6:               Q    V I
```

-continued

| | | |
|---|---|---|
| 51F7: | Q | V I |
| 52D11: | Q | V I |
| 52F2: | Q | V I |

EXAMPLE 2

Figure 8:
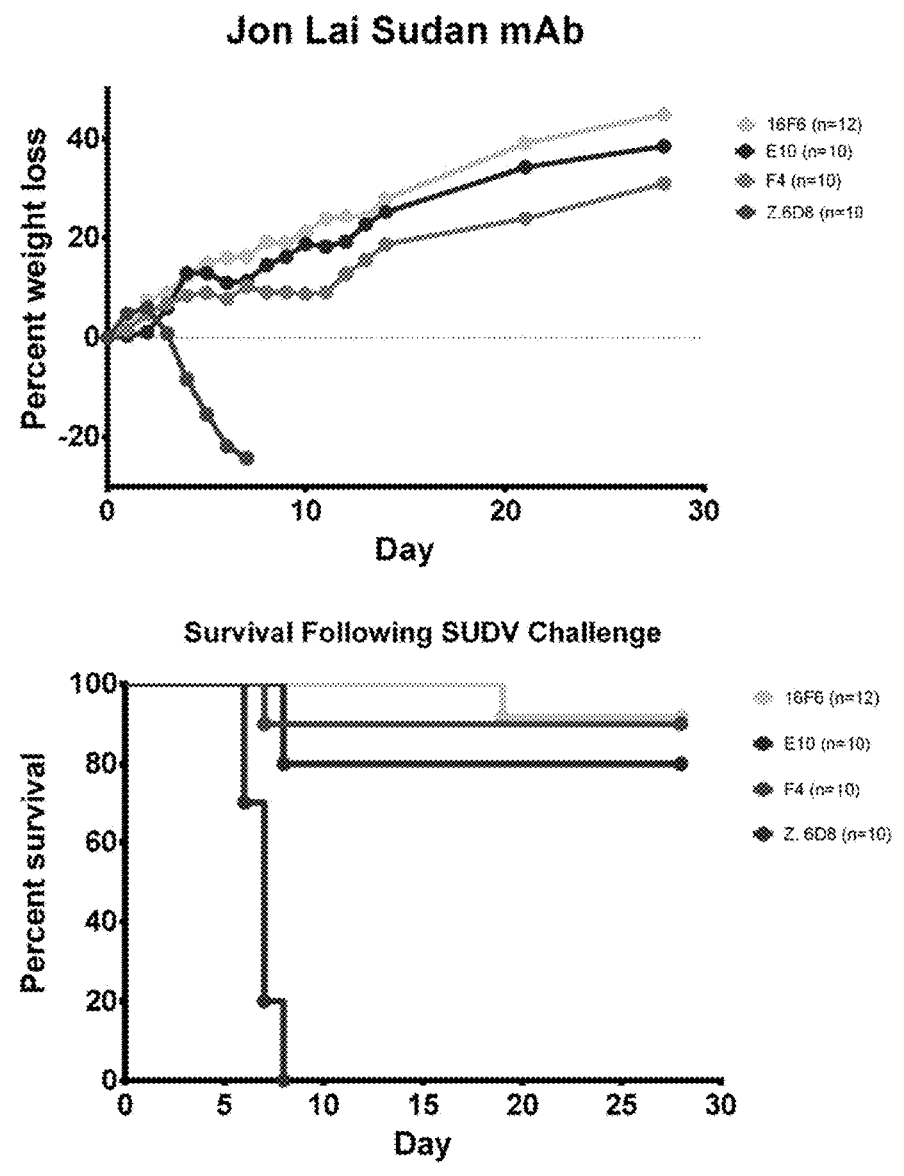
Figure 9:
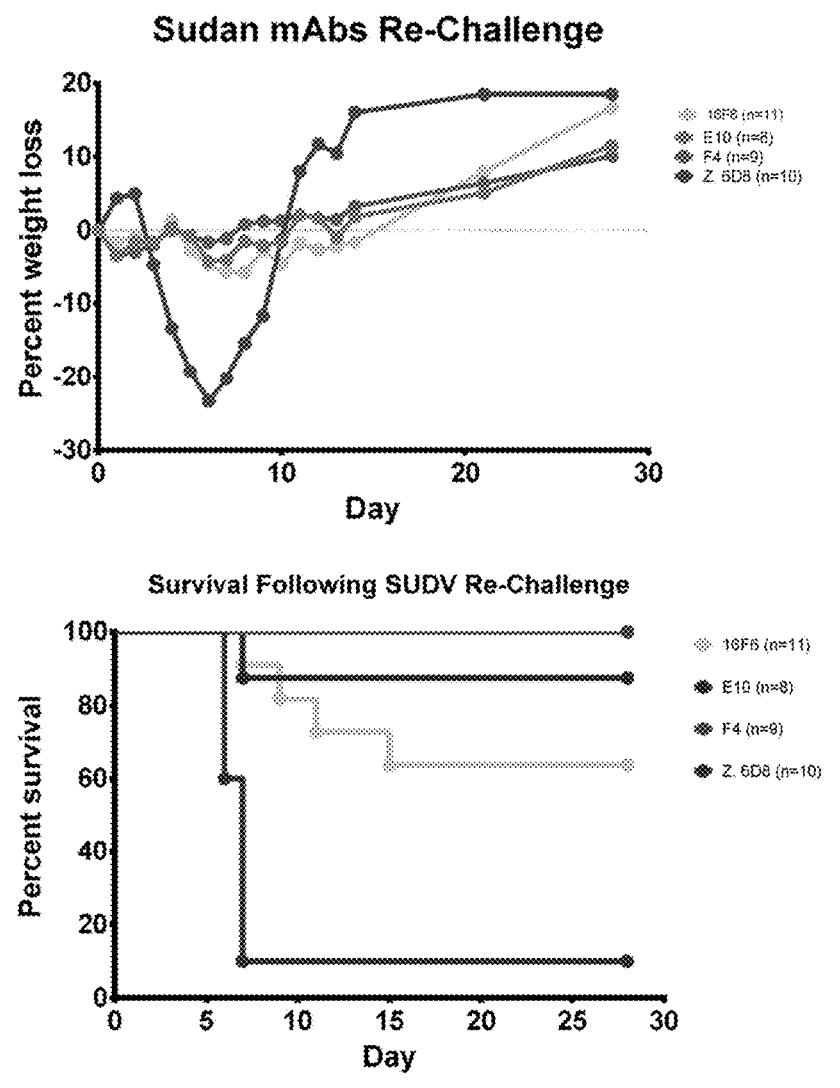
Figure 10:
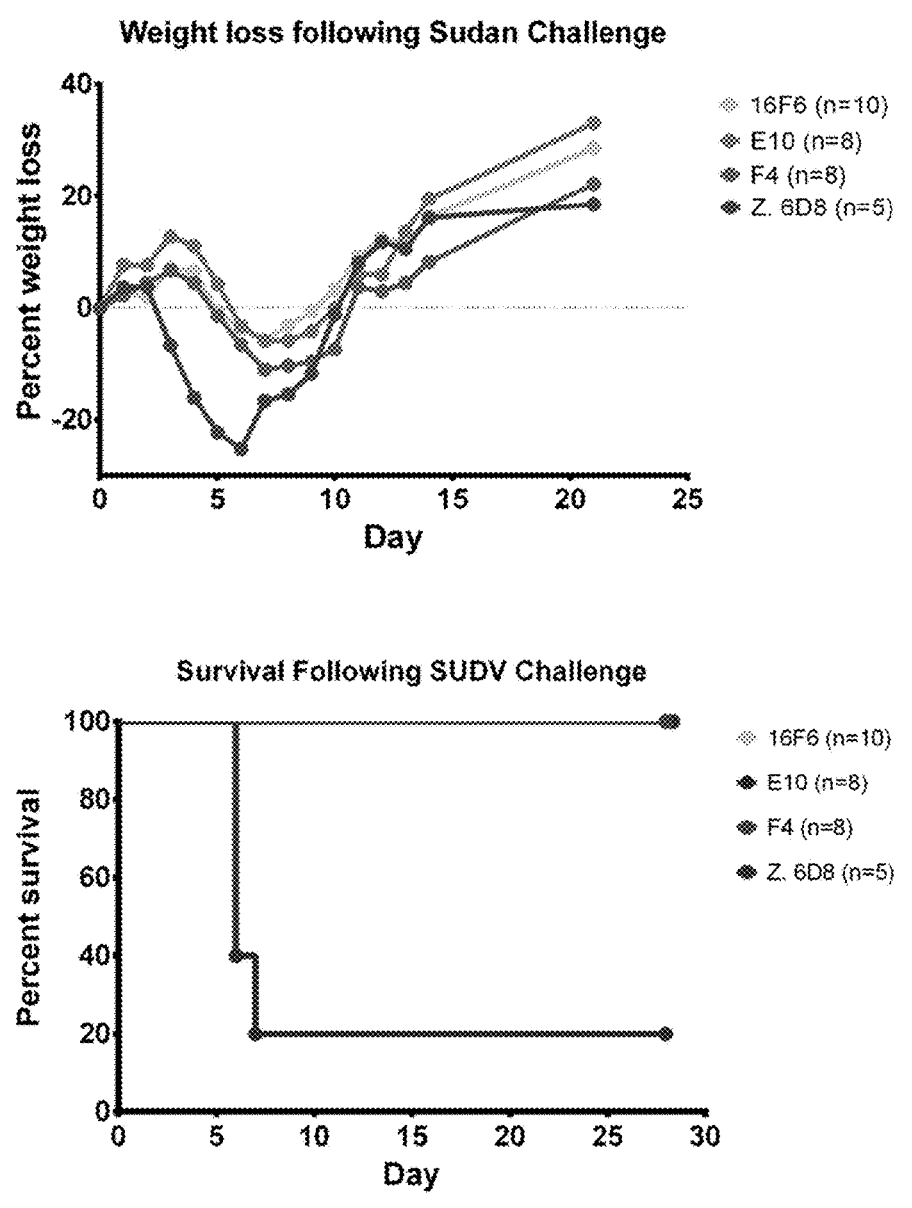

Challenge: Interferon alpha/beta KO mice were challenged with 1000 pfu of Sudan Ebola virus (SUDV). mAb was administered as described in each panel (See FIG. 8). 16F6 (murine) and 6D8 were included as positive and negative controls respectively. Mortality and weight change were monitored. Re-challenge: Surviving mice from the challenge experiment were re-challenged at day 28 without antibody (except the negative control 6D8) (See FIG. 9). Mice that survive the re-challenge have long-lasting immunity. (See FIGS. 8-10). (Antibodies E10 and F4 are encompassed by the invention. Antibodies 16F6 and 6D8 are positive and negative controls, respectively).

REFERENCES

1. Kuhn, J. H., Becker, S., Ebihara, H., Geisbert, T. W., Johnson, K. M., Kawaoka, Y., Lipkin, W. I., Negredo, A. I., Netesov, S. V., Nichol, S. T., Palacios, G., Peters, C. J., Tenorio, A., Volchkov, V. E., and Jahrling, P. B. (2010) Proposal for a revised taxonomy of the family Filoviridae: classification, names of taxa and viruses, and virus abbreviations. *Arch. Virol.* 155, 2083-2103.
2. Feldmann, H., and Gesibert, T. W. (2011) Ebola haemorrhagic fever. *Lancet* 9768, 849-862.
3. Miller, E. H., and Chandran, K. (2012) Filovirus entry into cells new insights. *Curr. Opin. Virol.* 2, 206-214.
4. Lee, J. E., and Saphire, E. O. (2009) Neutralizing ebolavirus: structural insights into the envelope glycoprotein and antibodies targeted against it. *Curr. Opin. Struct. Biol.* 19, 408-417.
5. Leroy, E. M., Kumulungui, B., Pourrut, X., Rouquet, P., Hassanin, A., Yaba, P., Delicat, A., Paweska, J. T., Gonzalez, J. P., and Swanepoel, R. (2005) Fruit bats as reservoirs of Ebola virus. *Nature* 438, 575-576.
6. http://www.cdc.gov/ncidod/dvrd/spb/mnpages/dispages/ebola.htm
7. Bradfute, S. B., Warfield, K. L., and Bavari, S. (2008) Functional CD8+ T cell responses in lethal Ebola virus infection. *J. Immunol.* 180, 4058-4066.
8. Zampieri, C. A., Sullivan, N. J., and Nabel, G. J. (2007) Immunopathology of highly virulent pathogens: insights from Ebola virus. *Nat. Immunol.* 8, 1159-1164.
9. Geisbert, T. W., Hensley, L. E., Larsen, T., Young, H. A., Reed, D. S., Geisbert, J. B., Scott, D. P., Kagan, E., Jahrling, P. B., and Davis, K. J. (2003) Pathogenesis of Ebola hemorrhagic fever in cynomolgus macaques: evidence that dendritic cells are early and sustained targets of infection. *Am. J. Pathol.* 163, 2347-2370.
10. Hensley, L. E., Jones, S. M., Feldmann, H., Jahrling, P. B., and Geisbert, T. W. (2005) Ebola and Marburg viruses: pathogenesis and development of countermeasures. *Curr. Mol. Med.* 5, 761-772.
11. Wilson, J. A., and Hart, M. K. (2001) Protection from Ebola virus mediated by cytotoxic T lymphocytes specific for the viral nucleoprotein. *J. Virol.* 75, 2660-2664.
12. Parren, P. W., Geisbert, T. W., Maruyama, T., Jahrling, P. B., and Burton, D. R. (2002) Pre- and postexposure prophylaxis of Ebola virus infection in an animal model by passive transfer of a neutralizing human antibody. *J. Virol.* 76, 6408-6412.
13. Lee, J. E., Fusco, M. L., Hessell, A. J., Oswald, W. B., Burton, D. R., and Saphire, E. O. (2008) Structure of the Ebola virus glycoprotein bound to an antibody from a human survivor. *Nature* 454, 177-182.
14. Dias, J. M., Kuehne, A. I., Abelson, D. M., Bale, S., Wong, A. C., Halfmann, P., Muhammad, M. A., Fusco, M. L., Zak, S. E., Kang, E., Kawaoka, Y., Chandran, K., Dye, J. M., and Saphire, E. O. (2011) A shared structural solution for neutralizing ebolaviruses. *Nat. Struct. Mol. Biol.* 18, 1424-1427.
15. Lee, J. E., and Saphire, E. O. (2009) Ebolavirus glycoprotein structure and mechanism of entry. *Future Virol.* 4, 621-635.
16. Weissenhorn, W., Carfi, A., Lee, K.-H., Skehel, J. J., and Wiley, D. C. (1998) Crystal structure of the Ebola virus membrane fusion subunit, GP2, from the envelope glycoprotein ectodomain. *Mol. Cell* 2, 605-616.
17. Malashkevich, V. N., Schneider, B. J., McNally, M. L., Milhollen, M. A., Pang, J. X., and Kim, P. S. (1999) Core structure of the envelope glycoprotein GP2 from Ebola virus at 1.9-Å resolution. *Proc. Natl. Acad. Sci. USA* 96, 2662-2667.
18. Harrison, J. S., Higgins, C. D., Chandran, K., and Lai, J. R. (2011) Designed protein mimics of the Ebola virus glycoprotein GP2 α-helical bundle: Stability and pH effects. *Protein Sci.* 20, 1587-1596.
19. Harrison, J. S., Koellhoffer, J. F., Chandran, K., and Lai, J. R. (2012) Marburg virus glycoprotein GP2: pH-dependent stability of the ectodomain α-helical bundle. *Biochemistry* 51, 2515-2525.
20. Oswald, W. B., Geisbert, T. W., Davis, K. J., Geisbert, J. B., Sullivan, N. J., Jahrling, P. B., Parren, P. W., and Burton, D. R. (2007) Neutralizing antibody fails to impact the course of Ebola virus infection in monkeys. *PLoS Pathog.* 3, e9.
21. Dye, J. M., Herbert, A. S., Kuehne, A. I., Barth, J. F., Muhammad, M. A., Zak, S. E., Ortiz, R. A., Prugar, L. I., and Pratt, W. D. (2012) Postexposure antibody prophylaxis protects nonhuman primates from Filovirus disease. *Proc. Natl. Acad. Sci. USA* 109, 5034-5039.
22. Marzi, A., Yoshida, R., Miyamoto, H., Ishijim, M., Suzuki, Y., Higuchi, M., Matsuyama, Y., Igarashi, M., Nakayama, E., Kuroda, M., Saijo, M., Feldmann, F., Brining, D., Feldmann, H., and Takada A. (2012) Protective efficacy of neutralizing monoclonal antibodies in a nonhuman primate model of Ebola hemorrhagic fever. *PLoS One* 7, e36192.
23. Wilson, J. A., Bosio, C. M., and Hart, M. K. (2001) Ebola virus: the search for vaccines and treatments. *Cell Mol. Life Sci.* 58, 1826-1841.
24. Sullivan, N. J., Martin, J. E., Graham, B. S., and Nabel, G. J. (2009) Correlates of protective immunity for Ebola vaccines: implications for regulatory approval by the animal rule. *Nat. Rev. Microbiol.* 7, 393-400.
25. Wilson, J. A., Hevey, M., Bakken, R., Guest, S., Bray, M., Schmaljohn, A. L., and Hart, M. K. (2000) Epitopes involved in antibody-mediated protection from Ebola virus. *Science* 287, 1664-1666.
26. Maruyama, T., Rodriguez, L. L., Jahrling, P. B., Sanchez, A., Khan, A. S., Nichol, S. T., Peters, C. J., Parren, P. W., and Burton, D. R. (1999) Ebola virus can be effectively neutralized by antibody produced in natural human infection. *J. Virol.* 73, 6024-6030.
27. Shurtleff, A. C., Warren, T. K., and Bavari, S. (2011) Non-human primates as models for the discovery and development of ebolavirus therapeutics. *Expert Opin. Drug Discov.* 6, 233-250.
28. Warfield, K. L., and Aman, M. J. (2011) Advances in virus-like particle vaccines for filoviruses. *J. Infect. Dis.* 204 *Suppl* 3, S1053-1059.
29. Fausther-Bovendo, H., Mulangu, S., and Sullivan, N. J. (2012) Ebolavirus vaccines for humans and apes. *Curr. Opin. Virol.* [Epub ahead of print] (May 3, PMID: 22560007)
30. Hoenen, T., Grosth, A., and Feldmann, H. (2012) Current ebola vaccines. *Expert Opin. Biol. Ther.* [Epub ahead of print] (May 5, PMID: 22559078)
31. Warren, T. K., Warfield, K. L., Wells, J., Swenson, D. L., Donner, K. S., Van Tongeren, S. A., Garza, N. L., Dong, L., Mourich, D. V., Crumley, S., Nichols, D. K., Iversen, P. L., and Bavari, S. (2010) Advanced antisense therapies for postexposure protection against lethal filovirus infections. *Nat. Med.* 16, 991-994.
32. Geisbert, T. W., Lee, A. C., Robbins, M., Geisbert, J. B., Honko, A. N., Sood, V., Johnson, J. C., de Jong, S., Tavakoli, I., Judge, A., Hensley, L. E., and Maclachlan, I. (2010) Postexposure protection of non-human primates against a lethal Ebola virus challenge with RNA interference: a proof-of-concept study. *Lancet* 375, 1896-1905.
33. Panchal, R. G., Reid, S. P., Tran, J. P., Bergeron, A. A., Wells, J., Kota, K. P., Aman, J., and Bavari, S. (2012) Identification of an antioxidant small-molecule with broad-spectrum antiviral activity. *Antiviral Res.* 93, 23-29.
34. Côté, M., Misasi, J., Ren, T., Bruchez, A., Lee, K., Filone, C. M., Hensley, L., Li, Q., Ory, D., Chandran, K., and Cunningham, J. (2011) Small molecule inhibitors reveal Niemann-Pick C1 is essential for Ebola virus infection. *Nature* 477, 344-348.
35. Basu, A., Li, B., Mills, D. M., Panchal, R. G., Cardinale, S. C., Butler, M. M., Peet, N. P., Majgier-Baranowska, H., Williams, J. D., Patel, I., Moir, D. T., Bavari, S., Ray, R., Farzan, M. R., Rong, L., and Bowlin, T. L. (2011) Identification of a small-molecule entry inhibitor for filoviruses. *J. Virol.* 85, 3106-3119.
36. Dimitrov, D. S., and Marks, J. D. (2009) Therapeutic antibodies: current state and future trends—is a paradigm change coming soon? *Methods Mol. Biol.* 525, 1-27.
37. Lerner, R. A., Kang, A. S., Bain, J. D., Burton, D. R., and Barbas, C. F. (1992) Antibodies without immunization. *Science* 258, 1313-1314.
38. Sidhu, S. S., and Fellouse, F. A. Synthetic therapeutic antibodies. (2006) *Nat. Chem. Biol.* 2, 682-688.
39. Winter, G. (1998) Synthetic human antibodies and a strategy for protein engineering. *FEBS Lett.* 430, 92-94.
40. Lerner, R. A. (2006) Manufacturing immunity to disease in a test tube: the magic bullet realized. *Angew. Chem. Int. Ed. Engl.* 48, 8106-8125.
41. Fellouse, F. A., Esaki, K., Birtalan, S., Raptis, D., Cancasci, V. J., Koide, A., Jhurani, P., Vasser, M., Wiesmann, C., Kossiakoff, A. A., Koide, S., and Sidhu, S. S. (2007) High-throughput generation of synthetic antibodies from highly functional minimalist phage-displayed libraries. *J. Mol. Biol.* 373, 924-940.
42. Fellouse, F. A., Li, B., Compaan, D. M., Peden, A. A., Hymowitz, S. G., and Sidhu, S. S. (2005) Molecular recognition by a binary code. *J. Mol. Biol.* 348, 1153-1162.
43. Liu, Y., Regula, L. K., Stewart, A., Lai, J. R. (2011) Synthetic Fab fragments that bind the HIV-1 gp41 heptad repeat regions. *Biochem. Biophys. Res. Commun.* 413, 611-615.
44. Ye, J. D., Tereshko, V., Frederiksen, J. K., Koide, A., Fellouse, F. A., Sidhu, S. S., Kossiakoff, A. A., and Piccirilli, J. A. (2008) Synthetic antibodies for specific recognition and crystallization of structured RNA. *Proc. Natl. Acad. Sci. USA* 105, 82-87.
45. Gao, J., Sidhu, S. S., and Wells, J. A. (2009) Two-state selection of conformation-specific antibodies. *Proc. Natl. Acad. Sci. USA* 106, 3071-3076.
46. Bostrom, J., Yu, S. F., Kan, D., Appleton, B. A., Lee, C. V., Billeci, K., Man, W., Peale, F., Ross, S., Weismann, C., and Fuh, G. (2009) Variants of the antibody Herceptin that interact with HER2 and VEGF at the antigen binding site. *Science* 323, 1610-1614.
47. Chandran, K., Sullivan, N. J., Felbor, U., Whelan, S. P., and Cunningham, J. M. (2005) Endosomal proteolysis of the Ebola virus glycoprotein is necessary for infection. *Science* 308, 1643-1645.
48. Fellouse, F. A., Wiesmann, C., and Sidhu, S. S. (2004) Synthetic antibodies from a four-amino-acid code: A dominant role for Tyrosine in antigen recognition. *Proc. Natl. Acad. Sci. USA* 101, 12467-12472.
49. Bostrom, J., Lee, C. V., Haber, L., and Fuh, G. Chapter 19: Improving antibody binding affinity and specificity for therapeutic development. In "Therapeutic Antibodies: Methods and Protocols", vol 525, Dimitrov, A. S. (Ed). 2009. Humana Press: New York, N.Y. Pp 353-376.
50. Pal, G., Kouadio, J. L., Artis, D. R., Kossiakoff, A. A., and Sidhu, S. S. (2006) Comprehensive and quantitative mapping of energy landscapes for protein-protein interactions by rapid combinatorial scanning. *J. Biol. Chem.* 281, 22378-22385.
51. Pal, G., Fong, S. Y., Kossiakoff, A. A., and Sidhu, S. S. (2005) Alternative views of functional protein binding epitopes obtained by combinatorial shotgun scanning mutagenesis. *Protein Sci.* 14, 2405-2413.
52. Weiss, G. A., Watanabe, C. K., Zhong, A., Goddard, A., and Sidhu, S. S. (2000) Rapid mapping of protein functional epitopes by combinatorial alanine scanning. *Proc. Natl. Acad. Sci. USA* 97, 8950-8954.
53. Vajdos, F. F., Adams, C. W., Breece, T. N., Presta, L. G., de Vos, A. M., and Sidhu, S. S. (2002) Comprehensive functional maps of the antigen-binding site of an anti-ErbB2 antibody obtained with shotgun scanning mutagenesis. *J. Mol. Biol.* 320, 415-428.
54. Da Silva, G. F., Harrison, J. S., and Lai, J. R. (2010) Contribution of light chain residues to high affinity binding in an HIV-1 antibody explored by combinatorial scanning mutagenesis. *Biochemistry* 49, 5464-5472.
55. Clackson, T., and Wells, J. A. (1995) A hot spot of binding energy in a hormone-receptor interface. *Science* 267, 383-386.
56. Kouadio, J. L., Horn, J. R., Pal, G., and Kossiakoff, A. A. (2005) Shotgun alanine scanning shows that growth hormone can bind productively to its receptor through a drastically minimized interface. *J. Biol. Chem.* 280, 25524-25532.

57. Mazor, Y., Barnea, I., Keydar, I., and Benhar, I. (2007) Antibody internalization studied using a novel IgG binding toxin fusion. *J. Immunol. Methods* 321, 41-59.

58. Phoolcharoen, W., Dye, J. M., Kilbourne, J., Piensook, K., Pratt, W. D., Arntzen, C. J., Chen, Q., Mason, H. S., Herbst-Kralovetz, M. M. (2011) A nonreplicating subunit vaccine protects mice against lethal Ebola virus challenge. *Proc. Natl. Acad. Sci. USA* 108, 20695-20700.

What is claimed:

1. An isolated humanized anti-Filovirus glycoprotein prefusion core antibody comprising a framework region having a sequence of 95% or greater identity to a human antibody framework region, and comprising
    (a) a heavy chain CDR1 comprising GFAFNYYDMH (SEQ ID NO:1); a heavy chain CDR2 comprising YINPGGGNTYYADSV (SEQ ID NO:2); and a heavy chain CDR3 comprising QLYGNSFMDY (SEQ ID NO:3), and
    (b) a light chain sequence DIQMTQSPSSLSAS-VGDRVTITCQASQDVTTAVAWYQQKPGKAPKL (SEQ ID NO:12) comprising a light chain CDR1, a light chain sequence LIYAASGRHKGVPSRFSGSGS-GTDFTLTISSLQPEDFATYYCQQ (SEQ ID NO:13) comprising a light chain CDR2, and a light chain CDR3 comprising HYSTPLT (SEQ ID NO:5).

2. The humanized antibody of claim 1, wherein the heavy chain comprises the sequence EVQLVESGGGLVQPGGSL-RLSCAASGFAFNYYDMHWVRQAPGKGLE (SEQ ID NO:8).

3. The humanized antibody of claim 1, wherein the heavy chain comprises the sequence WVAYINPGGGNTYYADS-VKGRFTISADTSKNTAYLQMNSLRAEDTA (SEQ ID NO:9).

4. The humanized antibody of claim 1, wherein the heavy chain comprises the sequence VYYCARQLYGNSFMDY-WGQGTLVTV (SEQ ID NO:10).

5. The humanized antibody of claim 1, wherein the light chain comprises the sequence HYSTPLTFGQGTKVFI (SEQ ID NO:16).

6. An antigen-binding fragment of the antibody of claim 1.

7. A composition comprising the antibody of claim 1 or an antigen-binding fragment thereof.

8. The composition of claim 7, comprising a pharmaceutically acceptably carrier.

9. A method of inhibiting an Ebola virus infection of a subject comprising administering to the subject an amount of the antibody of claim 1 or an antigen-binding fragment thereof effective to inhibit an Ebola virus infection in a subject, wherein administration is prior to the subject being exposed to the Ebola virus, further wherein the Ebola virus is the Sudan strain.

* * * * *

```
                          SEQUENCE LISTING

<160> NUMBER OF SEQ ID NOS: 34

<210> SEQ ID NO 1
<211> LENGTH: 10
<212> TYPE: PRT
<213> ORGANISM: mouse sp.
<220> FEATURE:
<221> NAME/KEY: MISC_FEATURE
<222> LOCATION: (9)..(9)
<223> OTHER INFORMATION: x = M, I or L

<400> SEQUENCE: 1

Gly Phe Ala Phe Asn Tyr Tyr Asp Xaa His
1               5                   10

<210> SEQ ID NO 2
<211> LENGTH: 15
<212> TYPE: PRT
<213> ORGANISM: mouse sp.

<400> SEQUENCE: 2

Tyr Ile Asn Pro Gly Gly Gly Asn Thr Tyr Tyr Ala Asp Ser Val
1               5                   10                  15

<210> SEQ ID NO 3
<211> LENGTH: 10
<212> TYPE: PRT
<213> ORGANISM: mouse sp.

<400> SEQUENCE: 3

Gln Leu Tyr Gly Asn Ser Phe Met Asp Tyr
1               5                   10

<210> SEQ ID NO 4
<211> LENGTH: 10
<212> TYPE: PRT
<213> ORGANISM: mouse sp.

<400> SEQUENCE: 4

Gln Leu Tyr Gly Asn Ser Phe Phe Asp Tyr
1               5                   10

<210> SEQ ID NO 5
<211> LENGTH: 7
<212> TYPE: PRT
<213> ORGANISM: mouse sp.

<400> SEQUENCE: 5

His Tyr Ser Thr Pro Leu Thr
1               5

<210> SEQ ID NO 6
<211> LENGTH: 46
<212> TYPE: PRT
<213> ORGANISM: mouse sp.

<400> SEQUENCE: 6

Glu Val Gln Leu Val Glu Ser Gly Gly Gly Leu Val Gln Pro Gly Gly
1               5                   10                  15
```

```
Ser Leu Arg Leu Ser Cys Ala Ala Ser Gly Phe Ala Phe Asn Tyr Tyr
            20                  25                  30

Asp Ile His Trp Val Arg Gln Ala Pro Gly Lys Gly Leu Glu
        35                  40                  45

<210> SEQ ID NO 7
<211> LENGTH: 46
<212> TYPE: PRT
<213> ORGANISM: mouse sp.

<400> SEQUENCE: 7

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ala Phe Asn Tyr Tyr
            20                  25                  30

Asp Leu His Trp Val Arg Gln Ala Pro Gly Lys Gly Leu Glu
        35                  40                  45

<210> SEQ ID NO 8
<211> LENGTH: 46
<212> TYPE: PRT
<213> ORGANISM: mouse sp.

<400> SEQUENCE: 8

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ala Phe Asn Tyr Tyr
            20                  25                  30

Asp Met His Trp Val Arg Gln Ala Pro Gly Lys Gly Leu Glu
        35                  40                  45

<210> SEQ ID NO 9
<211> LENGTH: 46
<212> TYPE: PRT
<213> ORGANISM: mouse sp.

<400> SEQUENCE: 9

Trp Val Ala Tyr Ile Asn Pro Gly Gly Gly Asn Thr Tyr Tyr Ala Asp
1               5                   10                  15

Ser Val Lys Gly Arg Phe Thr Ile Ser Ala Asp Thr Ser Lys Asn Thr
            20                  25                  30

Ala Tyr Leu Gln Met Asn Ser Leu Arg Ala Glu Asp Thr Ala
        35                  40                  45

<210> SEQ ID NO 10
<211> LENGTH: 25
<212> TYPE: PRT
<213> ORGANISM: mouse sp.

<400> SEQUENCE: 10

Val Tyr Tyr Cys Ala Arg Gln Leu Tyr Gly Asn Ser Phe Met Asp Tyr
1               5                   10                  15

Trp Gly Gln Gly Thr Leu Val Thr Val
            20                  25

<210> SEQ ID NO 11
<211> LENGTH: 25
<212> TYPE: PRT
<213> ORGANISM: mouse sp.

<400> SEQUENCE: 11
```

Val Tyr Tyr Cys Ala Arg Gln Leu Tyr Gly Asn Ser Phe Phe Asp Tyr
1               5                   10                  15

Trp Gly Gln Gly Thr Leu Val Thr Val
            20                  25

<210> SEQ ID NO 12
<211> LENGTH: 46
<212> TYPE: PRT
<213> ORGANISM: mouse sp.
<220> FEATURE:
<221> NAME/KEY: MISC_FEATURE
<222> LOCATION: (24)..(24)
<223> OTHER INFORMATION: Xaa = Lys, Arg or gln

<400> SEQUENCE: 12

Asp Ile Gln Met Thr Gln Ser Pro Ser Ser Leu Ser Ala Ser Val Gly
1               5                   10                  15

Asp Arg Val Thr Ile Thr Cys Xaa Ala Ser Gln Asp Val Thr Thr Ala
            20                  25                  30

Val Ala Trp Tyr Gln Gln Lys Pro Gly Lys Ala Pro Lys Leu
        35                  40                  45

<210> SEQ ID NO 13
<211> LENGTH: 44
<212> TYPE: PRT
<213> ORGANISM: mouse sp.

<400> SEQUENCE: 13

Leu Ile Tyr Ala Ala Ser Gly Arg His Lys Gly Val Pro Ser Arg Phe
1               5                   10                  15

Ser Gly Ser Gly Ser Gly Thr Asp Phe Thr Leu Thr Ile Ser Ser Leu
            20                  25                  30

Gln Pro Glu Asp Phe Ala Thr Tyr Tyr Cys Gln Gln
        35                  40

<210> SEQ ID NO 14
<211> LENGTH: 44
<212> TYPE: PRT
<213> ORGANISM: mouse sp.

<400> SEQUENCE: 14

Leu Ile Tyr Ala Ala Ser Arg Leu His Asn Gly Val Pro Ser Arg Phe
1               5                   10                  15

Ser Gly Ser Gly Ser Gly Thr Asp Phe Thr Leu Thr Ile Ser Ser Leu
            20                  25                  30

Gln Pro Glu Asp Phe Ala Thr Tyr Tyr Cys Gln Gln
        35                  40

<210> SEQ ID NO 15
<211> LENGTH: 44
<212> TYPE: PRT
<213> ORGANISM: mouse sp.

<400> SEQUENCE: 15

Leu Ile Tyr Ala Ala Ser Thr Arg His Thr Gly Val Pro Ser Arg Phe
1               5                   10                  15

Ser Gly Ser Gly Ser Gly Thr Asp Phe Thr Leu Thr Ile Ser Ser Leu
            20                  25                  30

Gln Pro Glu Asp Phe Ala Thr Tyr Tyr Cys Gln Gln
        35                  40

```
<210> SEQ ID NO 16
<211> LENGTH: 16
<212> TYPE: PRT
<213> ORGANISM: mouse sp.

<400> SEQUENCE: 16

His Tyr Ser Thr Pro Leu Thr Phe Gly Gln Gly Thr Lys Val Phe Ile
1               5                   10                  15

<210> SEQ ID NO 17
<211> LENGTH: 10
<212> TYPE: PRT
<213> ORGANISM: mouse sp.

<400> SEQUENCE: 17

Gly Phe Ala Phe Asn Tyr Tyr Asp Met Phe
1               5                   10

<210> SEQ ID NO 18
<211> LENGTH: 15
<212> TYPE: PRT
<213> ORGANISM: mouse sp.

<400> SEQUENCE: 18

Tyr Ile Asn Pro Gly Gly Gly Asn Thr Tyr Tyr Pro Asp Ser Val
1               5                   10                  15

<210> SEQ ID NO 19
<211> LENGTH: 10
<212> TYPE: PRT
<213> ORGANISM: mouse sp.

<400> SEQUENCE: 19

Gln Leu Tyr Gly Asn Ser Phe Phe Asp Tyr
1               5                   10

<210> SEQ ID NO 20
<211> LENGTH: 46
<212> TYPE: PRT
<213> ORGANISM: mouse sp.

<400> SEQUENCE: 20

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Thr Thr Ala
                20                  25                  30

Val Ala Trp Tyr Gln Gln Lys Pro Gly Lys Ala Pro Lys Leu
            35                  40                  45

<210> SEQ ID NO 21
<211> LENGTH: 44
<212> TYPE: PRT
<213> ORGANISM: mouse sp.

<400> SEQUENCE: 21

Leu Ile Tyr Ala Ala Ser Gly Arg Tyr Ile Gly Val Pro Ser Arg Phe
1               5                   10                  15

Ser Gly Ser Gly Ser Gly Thr Asp Phe Thr Leu Thr Ile Ser Ser Leu
                20                  25                  30

Gln Pro Glu Asp Phe Ala Thr Tyr Tyr Cys Gln Gln
            35                  40
```

```
<210> SEQ ID NO 22
<211> LENGTH: 44
<212> TYPE: PRT
<213> ORGANISM: mouse sp.

<400> SEQUENCE: 22

Leu Ile Tyr Ala Ala Ser Phe Leu His Arg Gly Val Pro Ser Arg Phe
1               5                   10                  15

Ser Gly Ser Gly Ser Gly Thr Asp Phe Thr Leu Thr Ile Ser Ser Leu
            20                  25                  30

Gln Pro Glu Asp Phe Ala Thr Tyr Tyr Cys Gln Gln
        35                  40

<210> SEQ ID NO 23
<211> LENGTH: 80
<212> TYPE: PRT
<213> ORGANISM: Homo sapiens

<400> SEQUENCE: 23

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asp Ile Tyr Asp Asp
            20                  25                  30

Asp Ile His Trp Val Arg Gln Ala Pro Gly Lys Gly Leu Glu Trp Val
        35                  40                  45

Ala Tyr Ile Ala Pro Ser Tyr Gly Tyr Thr Asp Tyr Ala Asp Ser Val
    50                  55                  60

Lys Gly Arg Phe Thr Ile Ser Ala Asp Thr Ser Lys Asn Thr Ala Tyr
65                  70                  75                  80

<210> SEQ ID NO 24
<211> LENGTH: 80
<212> TYPE: PRT
<213> ORGANISM: mouse sp.

<400> SEQUENCE: 24

Glu Val Gln Leu Val Glu Ser Gly Gly Gly Leu Val Thr Pro Gly Gly
1               5                   10                  15

Ser Leu Lys Leu Ser Cys Ala Ala Ser Gly Phe Ala Phe Asn Tyr Tyr
            20                  25                  30

Asp Met Phe Trp Val Arg Gln Asn Thr Glu Lys Arg Leu Glu Trp Val
        35                  40                  45

Ala Tyr Ile Asn Ser Gly Gly Gly Asn Thr Tyr Tyr Pro Asp Thr Val
    50                  55                  60

Lys Gly Arg Phe Thr Ile Ser Arg Asp Asn Ala Lys Lys Thr Leu Phe
65                  70                  75                  80

<210> SEQ ID NO 25
<211> LENGTH: 80
<212> TYPE: PRT
<213> ORGANISM: Artificial Sequence
<220> FEATURE:
<223> OTHER INFORMATION: human mouse chimera
<220> FEATURE:
<221> NAME/KEY: misc_feature
<222> LOCATION: (29)..(29)
<223> OTHER INFORMATION: Xaa can be any naturally occurring amino acid
<220> FEATURE:
<221> NAME/KEY: misc_feature
<222> LOCATION: (34)..(35)
<223> OTHER INFORMATION: Xaa can be any naturally occurring amino acid
<220> FEATURE:
<221> NAME/KEY: misc_feature
```

```
<222> LOCATION: (53)..(53)
<223> OTHER INFORMATION: Xaa can be any naturally occurring amino acid
<220> FEATURE:
<221> NAME/KEY: misc_feature
<222> LOCATION: (61)..(61)
<223> OTHER INFORMATION: Xaa can be any naturally occurring amino acid

<400> SEQUENCE: 25

Glu Asx Gln Leu Val Glu Ser Gly Gly Gly Leu Val Gln Pro Gly Gly
1               5                   10                  15

Ser Leu Arg Leu Ser Cys Ala Ala Ser Gly Phe Ala Xaa Asn Tyr Tyr
            20                  25                  30

Asp Xaa Xaa Trp Val Arg Gln Ala Pro Gly Lys Gly Leu Glu Trp Val
        35                  40                  45

Ala Tyr Ile Asn Xaa Gly Gly Gly Asn Thr Tyr Tyr Xaa Asp Ser Val
    50                  55                  60

Lys Gly Arg Phe Thr Ile Ser Ala Asp Thr Ser Lys Asn Thr Ala Tyr
65                  70                  75                  80

<210> SEQ ID NO 26
<211> LENGTH: 40
<212> TYPE: PRT
<213> ORGANISM: Homo sapiens

<400> SEQUENCE: 26

Leu Gln Met Asn Ser Leu Arg Ala Glu Asp Thr Ala Val Tyr Tyr Cys
1               5                   10                  15

Ser Arg Ser Ser Asp Ala Ser Tyr Ser Tyr Ser Ala Met Asp Tyr Trp
            20                  25                  30

Gly Gln Gly Thr Leu Val Thr Val
            35                  40

<210> SEQ ID NO 27
<211> LENGTH: 37
<212> TYPE: PRT
<213> ORGANISM: mouse sp.

<400> SEQUENCE: 27

Leu Gln Met Ser Ser Leu Arg Ser Glu Asp Thr Ala Met Tyr Tyr Val
1               5                   10                  15

Ala Arg Gln Leu Tyr Gly Asn Ser Phe Phe Asp Tyr Trp Gly Gln Gly
            20                  25                  30

Thr Ser Leu Thr Val
        35

<210> SEQ ID NO 28
<211> LENGTH: 37
<212> TYPE: PRT
<213> ORGANISM: Artificial Sequence
<220> FEATURE:
<223> OTHER INFORMATION: human mouse chimera
<220> FEATURE:
<221> NAME/KEY: misc_feature
<222> LOCATION: (17)..(17)
<223> OTHER INFORMATION: Xaa can be any naturally occurring amino acid
<220> FEATURE:
<221> NAME/KEY: misc_feature
<222> LOCATION: (25)..(26)
<223> OTHER INFORMATION: Xaa can be any naturally occurring amino acid

<400> SEQUENCE: 28

Leu Gln Met Asn Ser Leu Arg Ala Glu Asp Thr Ala Val Tyr Tyr Cys
1               5                   10                  15
```

```
Xaa Arg Gln Leu Tyr Gly Asn Ser Xaa Xaa Asp Tyr Trp Gly Gln Gly
                 20                  25                  30

Thr Leu Val Thr Val
        35

<210> SEQ ID NO 29
<211> LENGTH: 40
<212> TYPE: PRT
<213> ORGANISM: Homo sapiens

<400> SEQUENCE: 29

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ala Ser Tyr Ser Ser
                 20                  25                  30

Val Ala Trp Tyr Gln Gln Lys Pro
        35                  40

<210> SEQ ID NO 30
<211> LENGTH: 40
<212> TYPE: PRT
<213> ORGANISM: mouse sp.

<400> SEQUENCE: 30

Asp Ile Val Met Thr Gln Ser His Lys Phe Met Ser Thr Ser Val Gly
1               5                   10                  15

Asp Arg Val Thr Ile Thr Cys Lys Ala Ser Gln Asp Val Thr Thr Ala
                 20                  25                  30

Val Ala Trp Tyr Gln Gln Lys Pro
        35                  40

<210> SEQ ID NO 31
<211> LENGTH: 40
<212> TYPE: PRT
<213> ORGANISM: Artificial Sequence
<220> FEATURE:
<223> OTHER INFORMATION: human mouse chimera
<220> FEATURE:
<221> NAME/KEY: misc_feature
<222> LOCATION: (24)..(24)
<223> OTHER INFORMATION: Xaa can be any naturally occurring amino acid

<400> SEQUENCE: 31

Asp Ile Gln Met Thr Gln Ser Pro Ser Ser Leu Ser Ala Ser Val Gly
1               5                   10                  15

Asp Arg Val Thr Ile Thr Cys Xaa Ala Ser Gln Asp Val Thr Thr Ala
                 20                  25                  30

Val Ala Trp Tyr Gln Gln Lys Pro
        35                  40

<210> SEQ ID NO 32
<211> LENGTH: 65
<212> TYPE: PRT
<213> ORGANISM: Homo sapiens

<400> SEQUENCE: 32

Gly Lys Ala Pro Lys Leu Leu Ile Tyr Ala Ala Ser Tyr Leu Tyr Ser
1               5                   10                  15

Gly Val Pro Ser Arg Phe Ser Gly Ser Gly Ser Gly Thr Asp Phe Thr
                 20                  25                  30

Leu Thr Ile Ser Ser Leu Gln Pro Glu Asp Phe Ala Thr Tyr Tyr Cys
        35                  40                  45
```

```
Gln Ser Ser Ala Ser Pro Ala Thr Phe Gly Gln Gly Thr Lys Val Glu
    50                  55                  60
Ile
65

<210> SEQ ID NO 33
<211> LENGTH: 66
<212> TYPE: PRT
<213> ORGANISM: mouse sp.

<400> SEQUENCE: 33

Gly His Ser Pro Lys Leu Leu Ile Tyr Trp Ala Ser Thr Arg His Thr
1               5                   10                  15

Gly Val Pro Asp Arg Phe Thr Gly Ser Gly Ser Gly Thr Ala Phe Thr
            20                  25                  30

Leu Thr Leu Asn Ser Val Gln Ala Glu Asp Leu Ala Leu Tyr Tyr Cys
        35                  40                  45

Gln Gln His Tyr Ser Thr Pro Leu Thr Phe Gly Ala Gly Thr Lys Leu
    50                  55                  60

Glu Leu
65

<210> SEQ ID NO 34
<211> LENGTH: 66
<212> TYPE: PRT
<213> ORGANISM: Artificial Sequence
<220> FEATURE:
<223> OTHER INFORMATION: human mouse chimera
<220> FEATURE:
<221> NAME/KEY: misc_feature
<222> LOCATION: (13)..(16)
<223> OTHER INFORMATION: Xaa can be any naturally occurring amino acid

<400> SEQUENCE: 34

Gly Lys Ala Pro Lys Leu Leu Ile Tyr Trp Ala Ser Xaa Xaa Xaa Xaa
1               5                   10                  15

Gly Val Pro Ser Arg Phe Ser Gly Ser Gly Ser Gly Thr Asp Phe Thr
            20                  25                  30

Leu Thr Ile Ser Ser Leu Gln Pro Glu Asp Phe Ala Thr Tyr Tyr Cys
        35                  40                  45

Gln Gln His Tyr Ser Thr Pro Leu Thr Phe Gly Gln Gly Thr Lys Val
    50                  55                  60

Glu Ile
65
```